Figure 1:
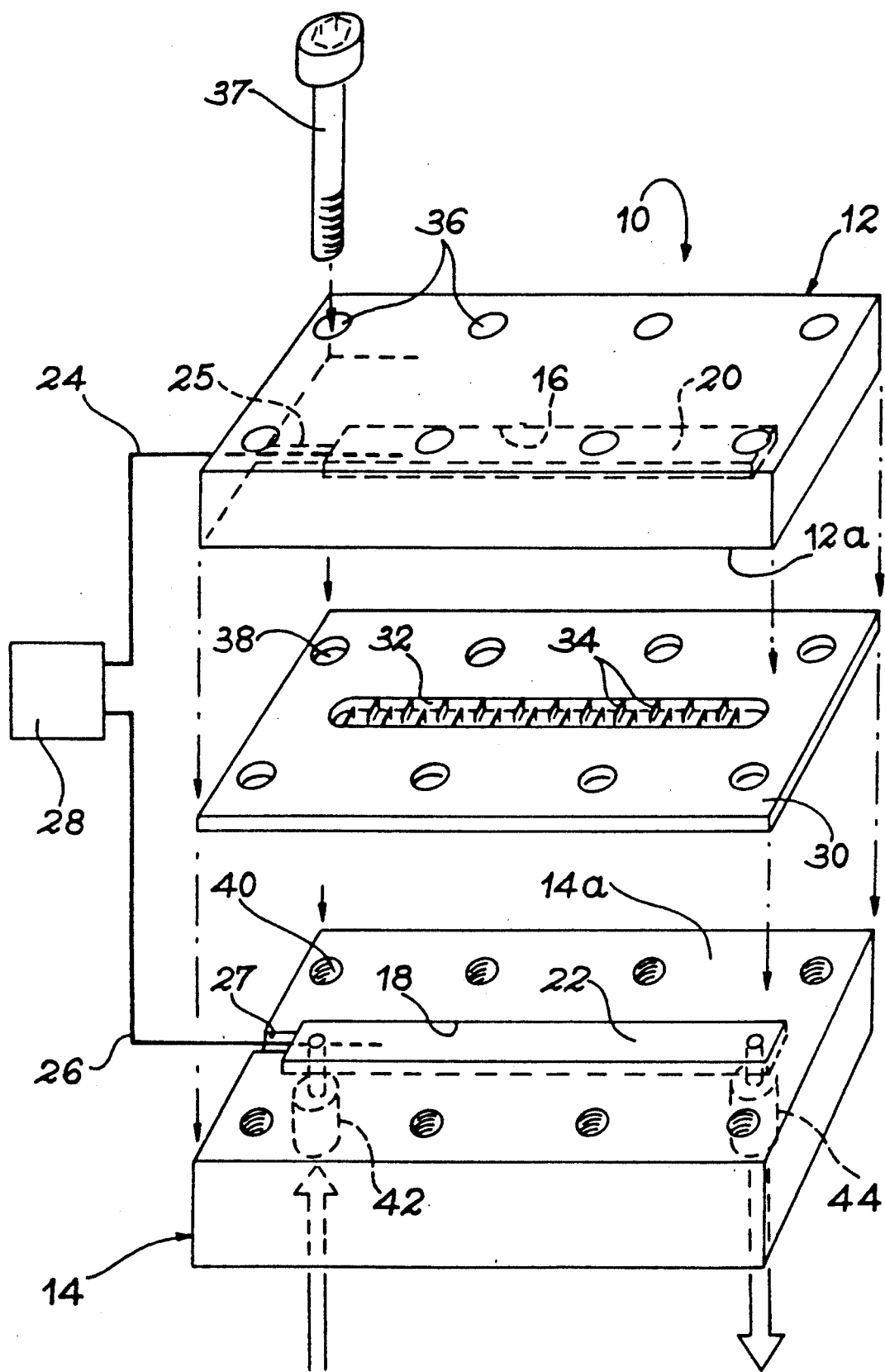

United States Patent [19]

Friconneau et al.

[11] Patent Number: 5,041,202

[45] Date of Patent: Aug. 20, 1991

[54] APPARATUS FOR THE CONTINUOUS PRODUCTION OF A STANDARD IONIC SOLUTION

[75] Inventors: Claude Friconneau; André Flaven, both of Manosque; Francis Granzotto, Pelissanne, all of France

[73] Assignee: Commissariat A l Energie Atomique, Paris, France

[21] Appl. No.: 550,378

[22] Filed: Jul. 10, 1990

[30] Foreign Application Priority Data

Jul. 17, 1989 [FR] France .................. 89 09580

[51] Int. Cl.$^5$ .................. C25B 9/00; C25B 15/08; G01N 27/26
[52] U.S. Cl. .................. 204/275; 204/405
[58] Field of Search .................. 204/275, 405

[56] References Cited

U.S. PATENT DOCUMENTS

| | | | |
|---|---|---|---|
| 2,864,750 | 12/1958 | Hughes, Jr. et al. | 204/275 X |
| 3,374,161 | 3/1968 | Zatz | 204/195 |
| 3,840,455 | 10/1974 | Cooley et al. | 204/275 X |
| 3,856,633 | 12/1974 | Fletcher et al. | 204/405 X |
| 3,966,413 | 6/1976 | Marineko | 23/253 |
| 4,053,377 | 10/1977 | Schlain et al. | 204/275 X |

FOREIGN PATENT DOCUMENTS 0039549 4/1981 European Pat. Off. .
2192139 5/1987 United Kingdom .

*Primary Examiner*—Donald R. Valentine
*Attorney, Agent, or Firm*—Hayes, Soloway, Hennessey & Hage

[57] ABSTRACT

This apparatus essentially comprises a coulometric cell (10) having an electrically insulating tight enclosure (12, 14, 30) containing a cathode (20) and an anode (22) which face one another and defining between them a space (21) for the passage of the solution to be enriched by said ions, a pipe (42) for supplying the solution to be enriched with ions and a pipe (44) for the discharge of the ion-enriched solution and issuing into said space (21), electric supply conductors (24, 26) for the cathode and the anode, the cathode and/or the anode containing said ions and being able to release them during the passage of the current and a current-stabilized electric supply source (28) connected to said conductors (24, 26).

14 Claims, 2 Drawing Sheets

APPARATUS FOR THE CONTINUOUS PRODUCTION OF A STANDARD IONIC SOLUTION

DESCRIPTION

The invention relates to an apparatus for the continuous production of a standard ionic solution in a very wide range of concentrations. This apparatus is in particular used in chains or cascades for measuring the concentration of certain ions in aqueous solution and in particular halide ions. Said apparatus can be integrated into the measuring chain or cascade and permits a reliable, precise, rapid and simple standardization or calibration of said measuring chain.

It is known that stainless steels are attacked or corroded by aqueous solutions containing halides, even if the latter are only present in a small quantity. In particular, chlorides can lead to significant damage to high pressure turbines. In addition, the main manufacturers of such turbines recommend that the chloride concentrations of the high pressure steam be kept below 5 ppb. It is also necessary to continuously detect the presence of chloride in water, even at very low concentrations.

The highest performance measuring chains for the continuous dosing or metering of chlorides require a monthly calibration. The latter usually involves the preparation of secondary standard solutions obtained by successive dilutions of a standard primary solution with demineralized water.

The highest performance equipment attempt to limit the operating phases external of the preparation of the primary standard solution by integrating certain functions, such as dilution, in the calibration apparatus. This integration leads to calibration apparatus, which are generally difficult to use.

Calibration by dilution involves disadvantages such as the limitation to low concentrations of the standard solutions, risks of error due to a sequence of interventions for introducing the primary or secondary standard solutions and the difficulty of handling demineralized water for a sufficiently low level chloride ion dilution.

The invention is directed at an apparatus for the continuous production of a standard ionic solution making it possible to obviate these disadvantages. In particular, the apparatus according to the invention makes it possible in a simple and rapid manner without any risk of error to obtain standard ionic solutions in a very wide concentration range and more specifically of chloride ions.

The principle of the invention is based on the coulometric production of ions at clearly defined concentrations in an aqueous solution flowing between two specific electrodes.

More specifically, the invention relates to an apparatus for the production of a standard ionic solution containing specific ions at a specific concentration, characterized in that essentially it comprises a coulometric cell having a tight, electrically insulating enclosure containing a cathode and an anode facing one another and defining between them a space for the passage of the solution to be enriched by said ions, pipes respectively for supplying the solution to be enriched with ions and for discharging the ion-enriched solutions, issuing into said space, electric supply conductors for the cathode and the anode, the cathode and/or the anode containing said ions and being able to release them during the passage of the current and a current-stabilized electric supply source connected to said conductors.

The apparatus according to the invention only makes it possible to produce ions during the application of a current to the electrodes. Any ion leaks linked solely with the solubility product of the electrodes in the solution is negligible.

The use according to the invention of a stabilized current supply makes it possible, bearing in mind the flow rate of the ionic solution between the two electrodes, to produce the ion quantity necessary for obtaining the chosen standard ionic solution. The quantity of ions released by the anode and/or cathode is a rising function of the intensity of the current.

The apparatus according to the invention makes it possible to produce a standard solution in a very wide range of concentrations between $10^{-7}$M (mole/l) to $10^{-3}$M with a good efficiency. The concentration of ions which it is possible to produce towards low levels (below $10^{-7}$M) using the apparatus according to the invention are well within the sensitivity range of the best known existing systems. Towards high concentrations (above $10^{-3}$M), the limits of the apparatus according to the invention are imposed by the shape and dimensions of the coulometric cell, the laws of coulometry and the redox potentials of the electrodes.

According to a preferred embodiment of the apparatus according to the invention, the enclosure is formed from two facing insulating support plates, which are respectively coated with the anode and the cathode and which are tightly assembled by their edges. Apart from their electrical insulation, these plates must be chemically resistant to the ionic solution to be produced. In the case of halide ions, these plates can be of polyvinyl chloride or plexiglass. Advantageously, each of the insulating plates is provided with a groove in which are respectively located the anode and the cathode.

A preferred constructional variant of the coulometric cell consists of intercalating between the two insulating support plates an intermediate plate made from an electrically insulating material and which is sufficiently elastic to constitute a sealing joint, said intermediate plate having, facing the anode and the cathode, a slot for the passage of the ionic solution. The insulating material constituting said plate can be silicone, polyethylene and in particular use is made of TEFLON, a synthetic resin polymer In order to homogenize the ions of the standard solution, the intermediate plate slot can have baffles.

In order to facilitate the fitting of the apparatus according to the invention, the support plates are planar and parallelepipedic and each of them is provided with a passage for the electric supply conductors of the electrodes.

The supply and discharge of the ionic solution from the inter-electrode space can be brought about by using two tubes traversing one or both support plates perpendicular to their surfaces. In other words, the supply and discharge of the solution from the coulometric cell can take place from the same side of the cell or on either side thereof.

According to the invention, the anode and/or cathode are made from consumable materials essentially containing the ions to form the standard solution.

In the particular case of producing a standard ionic solution containing halide ions, use is made of a cathode constituted by a compacted pellet containing a metal halide generally associated with a metallic powder. For example, for the production of chloride ions, use is made of a compacted pellet constituted by a silver powder and a silver chloride powder. In the same way, for the production of bromide ions and iodide ions, use is made of a compacted pellet containing silver and respectively silver bromide and silver iodide. In the same way, for the production of zinc ions and copper ions, respectively use is made of copper and zinc electrodes.

The different electrodes usable in the invention and specific to the ions to be produced are in particular those described in FR-A-2 203 518.

The production of a given ion type is a function of the voltage applied to the terminals of the electrodes, besides the nature of the electrodes themselves.

Moreover, the electrode associated with the consumable electrode is chosen in such a way as to avoid the production of disturbing ions, either by redox reaction, or by precipitation reaction, or by a gaseous release.

In the particular case of producing chloride ions from a chloride cathode in accordance with the reaction:

$$AgCl + e^- \rightarrow Ag^\circ + Cl^-$$

it is possible to use as the anode copper, gold, lead, platinum, tellurium dioxide ($TeO_2$), lead dioxide ($PbO_2$) and manganese dioxide ($MnO_2$). Preference is given to the use of a copper anode and the corresponding redox reaction is as follows:

$$Cu \rightarrow Cu^{2+} + 2e^-$$

In addition, the use of a copper anode makes it possible to produce $Cu^{2+}$ ions and therefore a standard $Cu^{2+}$ ion solution.

In order to avoid the decomposition of the water and therefore the production of ions other than those desired, the pH must be adjusted to an appropriate value. In the particular case of an AgCl production, use is made of a pH of 3.5 to 4 for chloride ion production.

The invention is described in greater detail hereinafter relative to non-limitative embodiments and with reference to the attached drawings, wherein show:

FIG. 1 Diagrammatically an exploded view of the apparatus according to the invention.

Figure 2:
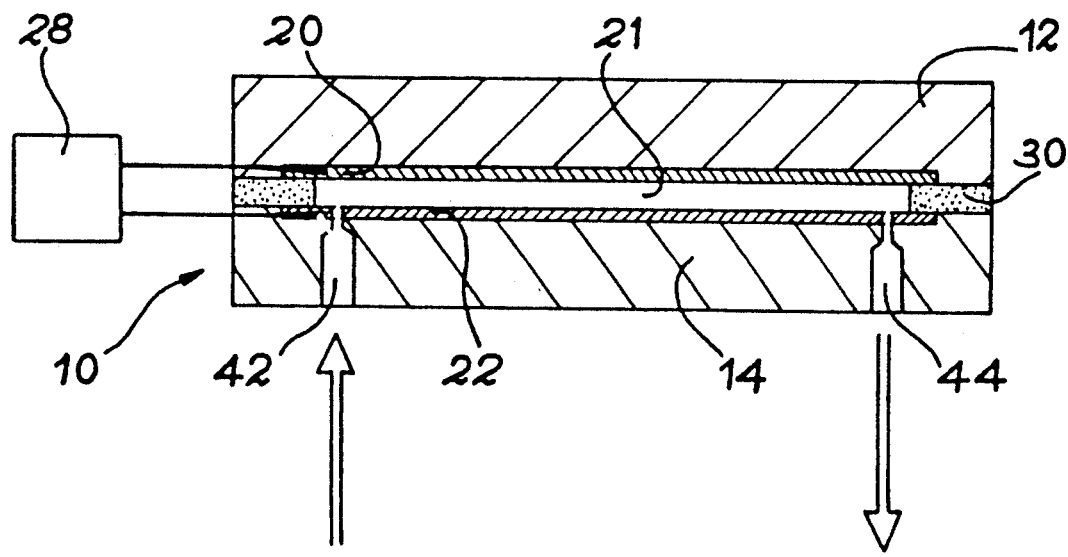

FIG. 2 Diagrammatically a longitudinal sectional view of the coulometric cell of FIG. 1.

Figure 3:
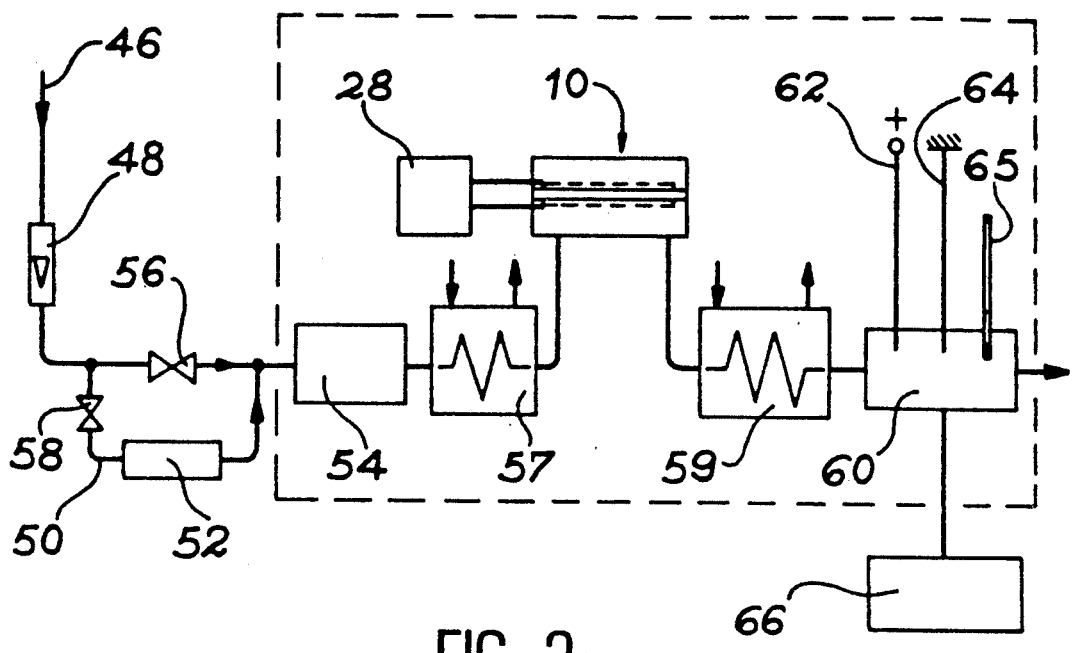

FIG. 3 Diagrammatically a chain for measuring chloride ions equipped with the apparatus of FIG. 1.

As shown in FIG. 1, the apparatus for producing a standard solution according to the invention comprises a coulometric cell 10 essentially having an upper support plate 12 made from an electrical insulating material and a lower support plate 14 also made from an electrical insulating material. These parallelepipedic support plates 12 and 14 are also made from a chemically inert material with respect to the ions to be produced. In the case of producing chloride ions, said plates are more particularly made from polyvinyl chloride (PVC).

The respective faces 12a and 14a of the plates 12 and 14, which are to face one another, are in each case equipped with an elongated groove 16 and 18, in which are respectively located a cathode 20 and an anode 22. These grooves 16 and 18 are made in the plates 12 and 14 in such a way that the cathode 20 and the anode 22 face one another during the assembly of the cell and as shown in FIG. 2.

For the production of chloride ions, the cathode 20 is e.g. constituted by a powder compacted in the form of an elongated plate containing 30% by weight of silver powder and 70% by weight of silver chloride. A metal wire 24, in particular of silver-covered platinum or silver and whereof one of the ends is embedded in the electrode material, makes it possible to supply the current to the electrode.

Moreover, the anode 22 is constituted, for the production of the chloride ions, by an elongated copper plate and a copper conductive wire 26, one of whose ends is welded to the copper plate so as to make it possible to supply current to the electrode 22.

A stabilized current electric supply source 28, whose intensity can be regulated, is connected via conductors 24 and 26 respectively to the cathode and the anode, passages 25 and 27 being respectively made in the plates 12 and 14 for ensuring the exit of the conductors 24 and 26 from the coulometric cell 10.

The cell according to the invention also has an intermediate, parallelepipedic, TEFLON plate 30 serving as a sealing joint during the assembly of the cell (FIG. 2). Said plate 30 has an elongated, central slot (oval or rectangular) to be positioned facing the anode and the cathode. This central slot 32 makes it possible to bring about a circulation of the standard solution to be produced and has baffles 34 aiding the homogenization thereof.

The support plates 12 and 14 and the intermediate plate 30 have perforations 36, 38, 40 for the passage of screws 37 for the assembly of the coulometric cell. Finally, the cell is provided with a supply tube 42 for the standard solution to be produced and a discharge tube 44 for the standard solution produced, said tubes issuing into the inter-electrode space 21.

In the embodiment shown in FIGS. 1 and 2, the said tubes 42 and 44 are located on the same side of the coulometric cell and in particular solely traverse the support plate 14.

The coulometric cell according to the invention is intended to function continuously with an ionic solution flowing continuously between the anode and the cathode. The flow rate of the standard solution to be produced defines the time during which the solution is present in the inter-electrode space 21. With a fixed passage time of the solution between the electrodes, the chloride ion quantity produced is only dependent on the intensity of the current applied to the electrodes (Faraday's law). It is therefore possible to plot, for each coulometric cell type and for a given ionic solution flow rate, the curve of chloride ion concentration variations as a function of the intensity. The chloride ion concentration for a given intensity can be proved by ion chromatography or by a volumetric method.

The presently manufactured apparatus ensures a 100% efficiency up to a $10^{-3}M$ chloride ion production.

In addition, the apparatus according to the invention has a long life without requiring any intervention on the part of the operator. This life is obviously a function of the concentration of ions produced and the size of the electrodes. With the presently produced model, it is possible to produce $10^{-4}M$ chloride ions in 24 hours.

The presently produced model has overall dimensions of $80 \times 40$ mm, a 1 mm inter-electrode space and electrode dimensions of $65 \times 10 \times 3$ mm.

Using this model and a 500 ml/h solution flow rate, the efficiency of the coulometric cell for the production of $Cl^-$ ions from a silver chloride cathode and a copper anode is 0.075M/ampere in the concentration range between $10^{-3}$ and $10^{-7}$M.

The apparatus according to the invention can be directly inserted in the ion measuring chain or cascade and in particular in a chloride ion measuring chain, such as that shown in FIG. 3.

In simplified form, said measuring chain comprises a pipe 46 for supplying the solution to be measured and which is equipped with a flowmeter 48 fixing the passage time of the standard solution in the inter-electrode space 21 of the coulometric cell 10. This supply pipe 46 is equipped with a bypass pipe 50 on which is mounted a deionization column 52. The latter makes it possible to obtain a demineralized water better than $18M\Omega$. cm at 25° C. on entering the measuring chain.

This bypass pipe makes it possible to produce the standard solution for calibrating the measuring chain. The valves 56 and 58 respectively mounted on the pipes 46 and 50 permit the passage either of the solution whose chloride ion concentration is to be measured, or the standard solution for the calibration of the measuring chain.

The measuring chain is equipped with an acidification device 54 necessary for the dosing of the chloride ions into the solution from the installation. This acidification device 54 also makes it possible, during the calibration of the measuring chain, to acidify the demineralized water from the pipe 50 with an acid not containing the ion to be produced in the coulometric cell 10 according to the invention and in the present case the chloride ion. More particularly use is made of an organic acid, such as acetic, formic or phosphoric acid. This acidification of the standard solution to be produced makes it possible to improve the electrical conductivity in the coulometric cell 10.

On leaving the acidification apparatus 54 and upstream of the cell 10 is provided a helical heat exchanger 57 making it possible to cool and stir the solution, whose ion concentration is to be measured, as well as cool the standard solution. In the same way, a helical heat exchanger 59 is positioned at the outlet from the coulometric cell 10.

The cooling of the solution to be dosed and the solution to be calibrated makes it possible to reduce the solubility of the electrodes and in the case of a chloride measuring chain the solubility of the cathode, thus increasing the sensitivity of the measuring electrode 62 and that of the coulometric cell. Thus, the solubility product of the electrodes varies with the temperature.

At the outlet from the heat exchanger 59 is provided the measuring or dosing vessel 60 in which is immersed a measuring electrode 62, whose constitution is a function of the ion to be measured and a reference electrode 64. For chlorides, the measuring electrode 62 is produced by TACUSSEL and is marketed under the reference PCLGSM and the reference electrode 64 is a silver chloride, calomel or mercury sulphate electrode.

A thermometer 65 makes it possible to measure the temperature of the solution to be calibrated and a millivoltmeter 66 measures the potential difference between the measuring electrode 62 and the reference electrode 64. The millivoltmeter reading makes it possible to determine the ion concentration of the solution from the installation.

For further details concerning the measurement of the quantity of chloride ions in an aqueous solution, reference can be made to FR-A-2 288 310.

With the aid of the apparatus according to the invention, it is possible to calibrate a measuring chain to a low level (calibration point at $3.10^{-7}$M and $15.10^{-7}$M with 1 calibration daily lasting 5 minutes per point for about 40 years).

The apparatus according to the invention can in particular be used in dosed addition methods.

We claim:

1. Apparatus for the production of a standard ionic solution containing halide ions at a specific concentration, said apparatus comprising, in combination:
   a coulometric cell having a tight, electrically insulating enclosure,
   a cathode comprising a compacted powder containing a metal and said halide and an anode operatively disposed within said enclosure, said cathode and anode facing one another and defining between them a space for the passage of the solution to be enriched by said ions,
   pipe means for supplying the solution to be enriched with said ions to said space,
   pipe means for discharging the solution, enriched with said ions from said space,
   electrical supply conductors for supplying an electrical current to said cathode and said anode, and
   current-stabilized electric supply source connected to said conductors.

2. Apparatus according to claim 1, wherein said enclosure comprises two facing, insulating support plates respectively coated with said cathode and said anode, wherein said support plates are tightly assembled by their edges.

3. Apparatus according to claim 2, wherein each said support plate further comprises a groove in which said cathode and said anode are respectfully located.

4. Apparatus according to claim 3, wherein said coulometric cell further comprises a third plate made from an electrical insulating material and sealingly disposed between said support plates, said third plate having a slot facing said cathode and said anode, and permitting passage of said solution.

5. Apparatus according to claim 4, wherein said intermediate plate further comprises baffles disposed within said slot for homogenizing the solution.

6. Apparatus according to claim 5, wherein said intermediate plate comprises a synthetic resin polymer.

7. Apparatus according to claim 3, wherein said enclosure comprises polyvinyl chloride.

8. Apparatus according to claim 2, wherein said coulometric cell further comprises a third plate made from an electrical insulating material and sealingly disposed between said support plates, said third plate having a slot facing said cathode and said anode, and permitting passage of said solution.

9. Apparatus according to claim 8, wherein said intermediate plate further comprises baffles disposed within said slot for homogenizing the solution.

10. Apparatus according to claim 8, wherein said intermediate plate comprises a synthetic resin polymer.

11. Apparatus according to claim 1, wherein said pipe means for supplying and discharging traverse at least one said support plate substantially perpendicular to its surface.

12. Apparatus according to claim 1, wherein said cathode comprises a silver powder and a silver halide powder.

13. Apparatus according to claim 1, wherein said enclosure comprises polyvinyl chloride.

14. Apparatus according to claim 1, wherein said anode comprises copper.

* * * * *